United States Patent [19]

Bost

[11] 3,946,030

[45] Mar. 23, 1976

[54] 2-MERCAPTOARYLTHIOAZOLE PRODUCTION

[75] Inventor: Howard W. Bost, Bartlesville, Okla.

[73] Assignee: Phillips Petroleum Company, Bartlesville, Okla.

[22] Filed: Aug. 1, 1974

[21] Appl. No.: 493,749

[52] U.S. Cl. ............................................... 260/306
[51] Int. Cl.$^2$ ......................................... C07D 277/72
[58] Field of Search ..................................... 260/306

[56] References Cited
UNITED STATES PATENTS
3,530,143   11/1970   Merlin ............................... 260/306

*Primary Examiner*—R. Gallagher
*Assistant Examiner*—Anne Marie T. Tighe

[57] ABSTRACT

An improved process for the production of 2-mercaptoarylthiazoles comprising reacting a primary aryl amine and sulfur with selected nitrogen-containing compounds including thiourea, urea, cyanamide, metal cyanamide salts, dicyanodiamide, ammonium thiocyanate, and the like, in the presence or absence of carbon disulfide.

11 Claims, No Drawings

2-MERCAPTOARYLTHIOAZOLE PRODUCTION

This invention relates to the production of 2-mercaptoarylthiazoles. In accordance with another aspect, this invention relates to the production of 2-mercaptoarylthiazoles by reacting a primary aryl amine and sulfur with at least one nitrogen-containing compound selected from thiourea, ammonium thiocyanate, cyanamide, or metal cyanamide salts. In accordance with still another aspect, this invention relates to the production of 2-mercaptoarylthiazoles by reacting a primary aryl amine with sulfur and carbon disulfide in the presence of thiourea, urea, cyanamide, metal cyanamide salts, or ammonium thiocyanate.

Accordingly, an object of this invention is to provide an improved process for the production of 2-mercaptoarylthiazoles.

Another object of this invention is to provide reaction modifiers which will increase the yield of 2-mercaptoarylthiazoles.

A further object of this invention is to provide a commercially feasible process for the production of 2-mercaptoarylthiazoles.

Another object of this invention is to provide a process whereby increased yields of 2-mercaptoarylthiazoles are realized.

Other objects, aspects, and the several advantages of the invention will be apparent to those skilled in the art upon reading the specification and the appended claims.

In accordance with the invention, it has been found that selected nitrogen-containing compounds, such as urea, thiourea, cyanamide, metal cyanamide salts, and ammonium thiocyanate, promote the reaction of primary aryl amines with sulfur in obtaining increased yields of desired thiazole products.

In accordance with one embodiment of the invention, 2-mercaptoarylthiazoles are produced in increased yields by reacting at least one primary aryl amine with sulfur and carbon disulfide in the presence of at least one of thiourea, urea, cyanamide, metal cyanamide salts, and ammonium thiocyanate.

In accordance with another embodiment of the invention, 2-mercaptoarylthiazoles are produced by reacting a primary aryl amine with sulfur and at least one of thiourea, cyanamide, metal cyanamide salts, and ammonium thiocyanate.

Primary aryl amines which are useful in the preparation of 2-mercaptoarylthiazoles are those containing a replacable hydrogen on a carbon atom adjacent to the carbon atom to which the amino group is bonded. Presently preferred primary aryl amines include aniline and alkyl-substituted anilines, as well as α- and β-naphthyl amines and alkyl-substituted α- and β-naphthyl amines wherein said alkyl substituents contain from one to six carbon atoms per group, wherein from zero to four such alkyl substituents are present in the aniline compounds and from zero to six such alkyl substituents are present in the naphthyl amine compounds, and wherein a carbon atom adjacent to the carbon atom to which the amino group is bonded is unsubstituted. The primary aryl amines will generally contain from six to about 16 carbon atoms per molecule.

Examples of useful primary aryl amines include aniline, o-toluidine, 2-ethylaniline, 4-isopropyl-2-methylaniline, o-hexylaniline, 2,3,4,5-tetramethylaniline, α-naphthylamine, β-naphthylamine, 3-methyl-α-naphthylamine, 6-isopropyl-β-naphthylamine, 7-hexyl-β-naphthylamine, 3,4,5,6,7,8-hexamethyl-β-naphthylamine, and the like.

Approximately stoichiometric amounts of aryl amine and sulfur are generally used (one mole of aryl amine per gram-atom of sulfur), although from 0.2 to 5 moles aryl amine per gram-atom of sulfur can be used.

In the embodiments in which carbon disulfide is used, approximately 1.2 mole carbon disulfide per mole of aryl amine is generally used although amounts ranging from 0.2 to 5 moles carbon disulfide per mole of aryl amine can be used.

In the embodiments in which urea, thiourea, cyanamide, metal cyanamide salts, or ammonium thiocyanate are used in conjunction with carbon disulfide, the amount of each of these additives generally used is half-molar with respect to aryl amine (0.5 mole of additive per mole of aryl amine) although quantities ranging from 0.01 to 5 moles of additive per mole of aryl amine can be employed if desired.

In the embodiments in which thiourea, cyanamide, metal cyanamide salts, or ammonium thiocyanate are used to react with the aryl amine and sulfur, these additives are generally used in the range 1.1 to 1.5 moles of additive per mole of aryl amine. However, within the scope of this invention are amounts ranging from 0.2 to 5 moles of additive per mole of aryl amine.

In view of the demonstrated operability of calcium cyanamide in this invention, it is concluded that the use of the chemically similar cyanamide itself, as well as other alkaline earth cyanamides and alkali metal cyanamides, should likewise be within the scope of this invention.

The selected nitrogen-containing additives or promoters of the invention can be generally described by the generic formulas

(I)

and

(II)

wherein X = N; Y = O, S, or NH; and Z = OR, SR, NH$_2$, NHR, or NR$_2$; wherein R is a hydrocarbyl radical selected from alkyl, aryl, or cycloalkyl radicals or combinations thereof such as aralkyl, alkaryl, and the like, said R groups containing from one to about eight carbon atoms per group. Compounds convertible to compounds of Formulas I and II under conditions of the invention are also within the scope of the invention.

Examples of compounds of Formula I useful in this invention include urea, thiourea, guanidine, methyl carbamate, 2-ethylhexyl carbamate, ethyl thionocarbamate, cyclohexyl thiolcarbamate, benzylurea, p-tolylurea, phenylthiourea, and the like. Cyanamide is a compound of Formula II which is useful in this invention. Compounds which are convertible to compounds of Formulas I or II under reaction conditions of the invention include calcium cyanamide, dicyanodiamide, and ammonium thiocyanate.

The above-described reactions are generally carried out at temperatures between 200° and 350°C. Higher temperatures usually result in extensive decomposition of product. The optimum temperature to be used is dependent upon the reactivity of the starting materials. The range 225° to 300°C is presently preferred in this invention.

Reaction pressures are generally autogenous. The temperatures employed and the generation of hydrogen sulfide in the reaction can increase the pressure within the reactor to 1,200 psig or more. It may also be desirable at times to pressurize the reactor prior to attaining reaction conditions with hydrogen sulfide or with an inert gas, for example, to maintain a substantial proportion of the reactants in the liquid phase.

The reaction time is dependent, to a large extent, upon the desired degree of reaction, the reactivity of the reactants, and the temperature employed. Generally, times in the range from 1 to 5 hours are adequate to produce the desired results.

Any convenient means of isolating and purifying the desired product can be used. Currently preferred is the practice of contacting the reaction mixture with aqueous base to dissolve the mercaptoarylthiazole, filtering to remove unreacted insoluble starting materials and by-products, heating while bubbling air through solution to distill volatile starting materials (such as aryl amine) and by-products, and to decolorize product, acidifying the solution with mineral acid to precipitate desired product and isolating said product by filtration.

In accordance with the invention, 2-mercaptoarylthiazoles of the formula $$\underset{\text{Ar}}{\diagdown}\overset{\text{S}}{\diagup}\text{—SH} \qquad (1)$$

which can be prepared by means of this invention include those in which Ar is an arylene or alkarylene divalent radical which is fused into a five-membered ring as shown in formula I. Ar is preferably phenylene or alkylphenylene as shown in formula I*a* or naphthylene or alkylnaphthylene as shown in formula I*b* wherein the R's are either alike or different and are alkyl groups containing one to six carbon atoms per group. The number of R groups in formula I*a* is

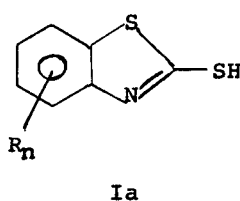

Ia

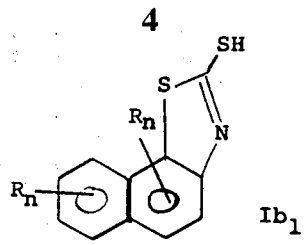

Ib₁

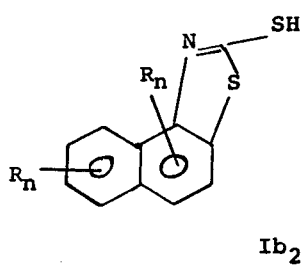

Ib₂

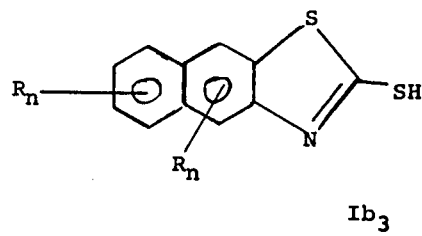

Ib₃ from 0 to 4 and in each of the formulas of I*b* is from 0 to 6. Compound I*a* will generally contain from seven to 13 carbon atoms per molecule and each of the compounds of I*b* will generally contain from 11 to 17 carbon atoms per molecule.

Examples of 2-mercaptoarylthiazoles which can be prepared by means of this invention are: 2-mercaptobenzothiazole, 2-mercapto-4-methylbenzothiazole, 5-ethyl-2-mercaptobenzothiazole, 6-isopropyl-2-mercapto-4-methylbenzothiazole, 4-hexyl-2-mercaptobenzothiazole, 2-mercapto-4,5,6,7-tetramethylbenzothiazole, 2-mercaptonaphtho(1,2-d)-thiazole, 2-mercaptonaphtho(2,1-d)thiazole, 2-mercaptonaphtho(2,3-d)-thiazole, 2-mercapto-4-methylnaphtho(1,2-d)thiazole, 7-isopropyl-2-mercaptonaphtho(2,3-d)thiazole, 8-hexyl-2-mercaptonaphtho(2,1-d)thiazole, 4,5,6,7,8,9-hexamethyl-2-mercaptonaphtho(2,1-d)thiazole, and the like.

It is recognized that compounds of formula I may exist partly or completely in the tautomeric form I' which

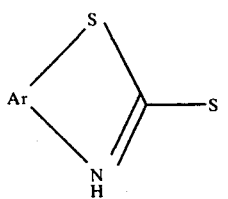

is the result of a proton shift from the mercapto group to the ring nitrogen. The tautomeric forms I or I', whether present wholly in one form or the other or as a mixture of the two, are within the scope of this invention.

2-Mercaptoarylthiazoles have been known in the art for many years as vulcanization accelerators. 2-Mercaptobenzothiazole, for example, has been commercially available for about 50 years for such an application.

EXAMPLE I

The following run (Run 1) illustrates the prior art process of preparing 2-mercapto-4-methylbenzothiazole from o-toluidine, carbon disulfide, and sulfur.

Into a 500 ml reactor were charged o-toluidine (27 g), sulfur (8g), and carbon disulfide (22 g). Seventy minutes of electrically heating the system was required to elevate the temperature to 275°C (240 psig original pressure at 275°C). After 2½ hours at 275°C (the pressure leveled out at 470 psig in 90 minutes) the heat source was removed and the reactor was cooled. The reaction mixture was mixed with 200 g water containing 16 g sodium hydroxide. Tar-like residue (18.5 g) was removed by decantation. Acidification of decantate with hydrochloric acid and filtration of the resulting mixture gave 21 g (46 percent yield) of crude 2-mercapto-4-methylbenzothiazole (m.p. 161°–173°C).

EXAMPLE II

The following invention run (Run 2) illustrates the benefits resulting from the use of thiourea with the prior art process described in Example I.

Into a 500 ml reactor were charged o-toluidine (54 g), sulfur (16 g), carbon disulfide (46 g), and thiourea (20 g). After 75 minutes of heating, 272°C and 280 psig were reached. During an additional 2½ hours heating at about 275°C the pressure rise leveled off at about 910–960 psig after 90 minutes. The cooled product mixture was dissolved in 400 g water containing 32 g sodium hydroxide. The very small amount of insoluble material was removed by filtration after which the filtrate was heated to boiling with a stream of air bubbling through it. Acidification of the cooled solution and filtration gave 72.8 g (79.6 percent yield) of dried yellow precipitate (m.p. 182°–186°C).

The use of thiourea gave nearly double the yield of 2-mercapto-4-methylbenzothiazole than obtained in the art process of Example I (80 vs. 46 percent).

EXAMPLE III

The following invention run (Run 3) illustrates the advantages resulting from use of urea with the art process described in Example I.

Into a 500 ml reactor were charged o-toluidine (54 g), sulfur (16 g), carbon disulfide (46 g), and urea (15 g). Ninety-five minutes heating was required for the system to reach the desired temperature — 272°C (475 psig). After 95 minutes heating at about 275°C the pressure rise leveled off at 1,110–1,130 psig. The system was heated at about 275°C for a total of 2½ hours. The cooled reaction mixture was washed with 400 ml water after which the solid residue was dissolved in 400 ml water containing 30 g sodium hydroxide. The alkaline solution was first extracted with 200 ml benzene and then heated to near boiling with an air stream bubbling through it. The cooled solution was then acidified with hydrochloric acid and the resultant precipitate was removed by filtration and dried. Crystals (56 g, 62 percent yield) were obtained which melted at 167°–174°C (softened at 163°C). Elemental analysis of the product showed 1.25 weight percent oxygen (probably residual water).

The use of urea improved the yield of 2-mercapto-4-methylbenzothiazole from 46 to 62 percent compared to the art process of Example I.

It should be noted that a duplicate run to Run 2 was made in which the alkaline solution was extracted with benzene at it was in Run 3. The resulting yield was 70 percent — 10 percent less than Run 2. Hence, elimination of the benzene extraction step from Run 3 could possibly increase the yield another 10 percent.

EXAMPLE IV

The following invention run (Run 4) illustrates the advantage resulting from use of ammonium thiocyanate with the art process described in Example I.

Run 4 was carried out as described in Example II except that ammonium thiocyanate (19 g) was used instead of thiourea. Time, temperature, pressure, and workup were nearly comparable to Run 2. Product (62.2 g, 69 percent yield) was obtained which melted at 168°–177°C.

The use of ammonium thiocyanate improved the yield of 2-mercapto-4-methylbenzothiazole from 46 to 69 percent compared to the art process of Example I.

EXAMPLE V

The following invention run (Run 5) illustrates the advantage resulting from use of thiourea as a replacement for carbon disulfide in the art process described in Example I.

Run 5 was carried out as described in Example II except that 57 g thiourea and no carbon disulfide were used. Time, temperature, pressure, and workup were nearly comparable to Run 2. Product (40 g, 44 percent yield) melting at 166°–175°C was obtained.

The use of thiourea as a replacement for carbon disulfide in the art process of Example I gave a yield of 2-mercapto-4-methylbenzothiazole comparable to that obtained in Run 1 (44 vs. 46 percent). The advantage of this inventive process is the elimination of the extremely hazardous carbon disulfide.

EXAMPLE VI

The following invention run (Run 6) illustrates the advantage resulting from use of ammonium thiocyanate as a replacement for carbon disulfide in the art process described in Example I.

Run 6 was carried out as described in Example II except that 42 g ammonium thiocyanate, 4.1 g hydrogen sulfide, and no carbon disulfide were used. The reaction was carried out for 2½ hours at 275°C with maximum pressure of 1,045 psig. The crude product mixture was a thick syrup rather than the usual solid mass. Alkali-insoluble material (8 g) was removed by filtration. Workup as described in Example II gave product (44 g, 48 percent yield) melting at 171°–175°C.

The use of ammonium thiocyanate as a replacement for carbon disulfide in the art process of Example I gave a yield of 2-mercapto-4-methylbenzothiazole comparable to that obtained in Run 1 (48 vs. 46 percent). The advantage of this inventive process is the elimination of the extremely hazardous carbon disulfide.

EXAMPLE VII

The following invention run (Run 7) illustrates the advantage resulting from use of calcium cyanamide with the art process described in Example I.

Run 7 was carried out as described in Example II except that calcium cyanamide (20 g) was used instead of thiourea. The system was heated at about 275°C for a total of 2.5 hours during which a maximum pressure of 715 psig was observed. Treatment of the cooled reaction mixture with aqueous base as described in Example II gave a considerable portion of solid material which was removed by filtration. Treatment of the filtrate and isolation of the resultant solid as described in Example II gave 47.5 g (52.7 percent yield) of product. Treatment of the originally removed solid with aqueous acid, following with filtration, treatment of the remaining solid with aqueous base, reprecipitation with aqueous acid, filtration, and washing and drying the resultant solid gave an additional 3 gm of product. The combined product represented a 56 percent yield of 2-mercapto-4-methylbenzothiazole melting at 164°C to 177°C.

The use of calcium cyanamide gave an improved yield of product compared to the art process of Example I (56 vs. 46 percent yield).

The data obtained in Runs 1 to 7 are tabulated in the following table.

| Run No. | o-Toluidine mole | Sulfur g-atom | Carbon Disulfide mole | Additive | Mole | Yield % |
|---|---|---|---|---|---|---|
| 1 | 0.25 | 0.25 | 0.29 | none | | 46 |
| 2 | 0.5 | 0.5 | 0.6 | thiourea | 0.25 | 80 |
| 3 | 0.5 | 0.5 | 0.6 | urea | 0.25 | 62[a] |
| 4 | 0.5 | 0.5 | 0.6 | ammonium thiocyanate | 0.25 | 69 |
| 5 | 0.5 | 0.5 | 0 | thiourea | 0.75 | 44 |
| 6 | 0.5 | 0.5 | 0 | ammonium thiocyanate | 0.55 | 48 |
| 7 | 0.5 | 0.5 | 0.6 | calcium cyanamide | 0.25 | 56 |

[a]-Alkaline solution extracted with benzene probably reducing recovered yield unnecessarily.

It can be concluded that thiourea, urea, calcium cyanamide, and ammonium thiocyanate improve the yield of 2-mercapto-4-methylbenzothiazole when added to the process described in the art. It can further be concluded that the extremely hazardous carbon disulfide of the process described in the art can be replaced with either thiourea or ammonium thiocyanate with no sacrifice in yield of product.

I claim:
1. A process for the production of 2-mercaptoarylthiazoles which comprises reacting
   a. at least one primary aryl amine having a replacable hydrogen on a carbon atom adjacent to the carbon atom to which the amino group is bonded selected from aniline, alkyl-substituted anilines, α- and β-naphthyl amines, and alkyl-substituted α- and β-naphthyl amines wherein the alkyl substituents contain from one to six carbon atoms per group and the primary aryl amine contains from six to 16 carbon atoms per molecule with
   b. sulfur and
   c. at least one nitrogen-containing compound having a formula selected from

and

wherein $Y = O$, $S$, or $NH$; and $Z = OR$, $SR$, $NH_2$, $NHR$, and $NR_2$; where R is a hydrocarbyl radical selected from alkyl, aryl, and cycloalkyl radicals having up to eight, inclusive, carbon atoms, and compounds selected from the group consisting of alkaline earth cyanamides, alkali metal cyanamides, dicyanodiamide, and ammonium thiocyanate which are convertible to compounds of Formulas I and II, under reaction conditions of a temperature in the range of 200°–350°C and a pressure up to 1,200 psig and in the presence of from 0.01 to 5 moles of nitrogen-containing compound per mole of primary aryl amine which produce 2-mercaptoarylthiazoles.

2. A process according to claim 1 wherein said reaction conditions include a temperature in the range of 225°–300°C.

3. A process according to claim 1 in which 2-mercaptoarylthiazoles are produced by reacting (a), (b), and (c) with (d) carbon disulfide wherein there is present from 0.2 to 5 moles aryl amine per gram-atom sulfur, from 0.2 to 5 moles of carbon disulfide per mole of aryl amine, and from 0.01 to 5 moles of nitrogen-containing compound per mole of primary aryl amine.

4. A process according to claim 1 in which 2-mercaptoarylthiazoles are produced by reacting (a), (b), and (c) with 0.2 to 5 moles aryl amine per gram-atom sulfur, and 0.2 to 5 moles of nitrogen-containing compound per mole of aryl amine being present during said reacting.

5. A process according to claim 23 for the production of 2-mercaptobenzothiazole which comprises reacting o-toluidine with sulfur, carbon disulfide, and thiourea.

6. A process according to claim 3 for the production of 2-mercaptobenzothiazole which comprises reacting o-toluidine with sulfur, carbon disulfide, and urea.

7. A process according to claim 3 for the production of 2-mercaptobenzothiazole which comprises reacting o-toluidine with sulfur, carbon disulfide, and ammonium thiocyanate.

8. A process according to claim 4 for the production of 2-mercaptobenzothiazole which comprises reacting o-toluidine with sulfur and thiourea.

9. A process according to claim 4 for the production of 2-mercaptobenzothiazole which comprises reacting o-toluidine with sulfur and ammonium thiocyanate.

10. A process according to claim 3 for the production of 2-mercaptobenzothiazole which comprises reacting o-toluidine with sulfur, carbon disulfide, and calcium cyanamide.

11. A process according to claim 1 wherein said reaction conditions include autogenous pressure.

* * * * *